US011123514B2

(12) United States Patent
Sardesai et al.

(10) Patent No.: US 11,123,514 B2
(45) Date of Patent: *Sep. 21, 2021

(54) APPARATUS AND METHOD TO PROVIDE BREATHING SUPPORT

(71) Applicants:Nolan Rajendra Sardesai, Arcadia, CA (US); Rangasamy Ramanathan, La Canada Flintridge, CA (US); Rajendra Gurudas Sardesai, Arcadia, CA (US)

(72) Inventors: Nolan Rajendra Sardesai, Arcadia, CA (US); Rangasamy Ramanathan, La Canada Flintridge, CA (US); Rajendra Gurudas Sardesai, Arcadia, CA (US)

(73) Assignee: Eupnea Technologies Inc., South Pasadena, CA (US)

( * ) Notice: Subject to any disclaimer, the term of this patent is extended or adjusted under 35 U.S.C. 154(b) by 378 days.

This patent is subject to a terminal disclaimer.

(21) Appl. No.: 16/168,494

(22) Filed: Oct. 23, 2018

(65) Prior Publication Data
US 2019/0054269 A1 Feb. 21, 2019

Related U.S. Application Data

(63) Continuation of application No. 15/139,020, filed on Apr. 26, 2016, now abandoned, which is a (Continued)

(51) Int. Cl.
*A61M 16/20* (2006.01)
*A61M 16/00* (2006.01)
*A61M 16/10* (2006.01)

(52) U.S. Cl.
CPC ...... *A61M 16/204* (2014.02); *A61M 16/0051* (2013.01); *A61M 16/024* (2017.08);
(Continued)

(58) Field of Classification Search
CPC .............. A61M 16/00; A61M 16/0009; A61M 16/0012; A61M 16/0051; A61M 16/0069;
(Continued)

(56) References Cited

U.S. PATENT DOCUMENTS 3,710,780 A 1/1973 Milch
3,811,671 A 5/1974 Turnbull
(Continued)

FOREIGN PATENT DOCUMENTS

DE 10322964 A1 12/2004
EP 0 234 736 A1 9/1987
(Continued)

OTHER PUBLICATIONS

Singhal, Nalini et al., "Newborn Resuscitation in Resource-Limited Settings" Seminars in Fetal & Neonatal Medicine, 2008, pp. 432-439, vol. 13.
(Continued)

*Primary Examiner* — Annette Dixon
(74) *Attorney, Agent, or Firm* — Rajendra Gurudas Sardesai

(57) ABSTRACT

A ventilator, or a breathing assistance apparatus, is provided to ventilate patients who may have breathing difficulties, the apparatus comprising a inspiratory pressure control duct; a positive end-expiratory pressure control duct; at least one valve connected to the peak inspiratory pressure control duct and to the positive end-expiratory pressure control duct, and at least one controller communicably connected to the valve to control rate of cycling of the valve, thereby controlling number of breaths per minute, and to control the duration of peak inspiratory pressure also known as inspiratory time.

20 Claims, 12 Drawing Sheets

Related U.S. Application Data continuation-in-part of application No. 14/468,320, filed on Aug. 25, 2014, now Pat. No. 9,345,850.

(60) Provisional application No. 61/929,947, filed on Jan. 21, 2014, provisional application No. 61/874,323, filed on Sep. 5, 2013.

(52) U.S. Cl.
CPC ........ *A61M 16/201* (2014.02); *A61M 16/202* (2014.02); *A61M 16/205* (2014.02); *A61M 16/209* (2014.02); *A61M 16/1045* (2013.01); *A61M 2016/0027* (2013.01); *A61M 2205/3334* (2013.01); *A61M 2205/3348* (2013.01); *A61M 2230/205* (2013.01)

(58) Field of Classification Search
CPC ............ A61M 16/0096; A61M 16/021; A61M 16/024; A61M 16/06; A61M 16/0633; A61M 16/0666; A61M 16/0683; A61M 16/08; A61M 16/0875; A61M 16/0883; A61M 16/20; A61M 16/201; A61M 16/202; A61M 16/204; A61M 16/205; A61M 16/209; A62B 9/02; B05B 15/65; B05C 5/001; B05C 5/0237; B05C 5/0258
USPC ............ 128/200.24, 201.23, 202.16, 202.22, 128/204.18, 204.21, 204.23, 204.24, 128/204.25, 204.26, 204.28, 205.11, 128/205.23, 205.24, 205.25
See application file for complete search history.

(56) References Cited

U.S. PATENT DOCUMENTS

| | | | |
|---|---|---|---|
| 3,827,433 A * | 8/1974 | Shannon | A61M 16/00 128/201.23 |
| 3,977,395 A | 8/1976 | Brawn | |
| 4,011,866 A | 3/1977 | Klein et al. | |
| 4,141,354 A * | 2/1979 | Ismach | A61M 16/021 128/204.26 |
| 4,459,983 A | 7/1984 | Beyreuther et al. | |
| 4,471,773 A | 9/1984 | Bunnell et al. | |
| 4,481,944 A | 11/1984 | Bunnell | |
| 4,679,551 A | 7/1987 | Anthony | |
| 4,805,612 A | 2/1989 | Jensen | |
| 4,838,259 A * | 6/1989 | Gluck | A61M 16/0096 128/204.21 |
| 4,941,469 A | 7/1990 | Adahan | |
| 5,156,776 A | 10/1992 | Loedding et al. | |
| 5,271,388 A | 12/1993 | Whitwam et al. | |
| 5,307,795 A | 5/1994 | Whitwam et al. | |
| 5,503,146 A * | 4/1996 | Froehlich | A61M 16/024 128/202.22 |
| 5,632,268 A | 5/1997 | Ellis et al. | |
| 5,752,506 A | 5/1998 | Richardson | |
| 6,086,822 A | 7/2000 | Trinidad | |
| 6,105,572 A | 8/2000 | Shaffer et al. | |
| 6,591,835 B1 | 7/2003 | Blanch | |
| 6,669,057 B2 * | 12/2003 | Saidman | B05C 5/001 222/146.5 |
| 6,805,120 B1 | 10/2004 | Jeffrey et al. | |
| 6,932,084 B2 * | 8/2005 | Estes | A61M 16/0051 128/204.18 |
| 7,077,154 B2 | 7/2006 | Jacobs et al. | |
| 7,191,780 B2 | 3/2007 | Faram | |
| 7,617,824 B2 * | 11/2009 | Doyle | A61M 16/0883 128/204.18 |
| 8,381,723 B2 | 2/2013 | DiBlasi et al. | |
| 8,499,759 B2 | 8/2013 | DiBlasi et al. | |
| 9,345,850 B2 * | 5/2016 | Sardesai | A61M 16/201 |
| 2004/0069304 A1 | 4/2004 | Jam | |
| 2005/0072470 A1 | 4/2005 | Jacobs et al. | |
| 2006/0078506 A1 | 4/2006 | Niven et al. | |
| 2007/0221116 A1 | 9/2007 | Kruse | |
| 2009/0056719 A1 | 3/2009 | Newman, Jr. | |
| 2011/0073112 A1 | 3/2011 | DiBlasi et al. | |
| 2011/0079222 A1 | 4/2011 | DiBlasi et al. | |
| 2016/0220779 A1 * | 8/2016 | Sardesai | A61M 16/201 |

FOREIGN PATENT DOCUMENTS

| | | |
|---|---|---|
| EP | 0 513 712 A1 | 11/1992 |
| WO | WO9710868 A1 | 3/1997 |
| WO | WO 2005/035019 A2 | 4/2005 |

OTHER PUBLICATIONS

Morley, C.J. et al., "Nasal Continous Positive Airway Pressure: Does Bubbling Improve Gas Exchange?" Arch Dis Child Fetal Neonatal Ed, 2005, pp. F343-F344, vol. 90.
Pillow, J. Jane et al., "Bubble Continuous Positive Airway Pressure Enhances Lung Volume and Gas Exchange in Preterm Lambs", Am J Resp Crit Care Med, 2007. pp. 63-69, vol. 176.
Reyburn, Brent et al., "Nasal Ventilation Alters Mesenchymal Cell Turnover and Improves Aleolarization in Preterm Lambs" Am J Resp & Crit Care Med, 2008, pp. 407-418, vol. 178.
Narasimhan, R. et al, "A Review of Non-Invasive Ventilation Support in Neonates" Paediatrics & Child Health, 2013, pp. 7-11, vol. 24, No. 1.
Lawn, Joy E. et al, "4 Million Neonatal Deaths. When? Where? Why?" Lancet, Mar. 2005, pp. 891-900. vol. 365.
Koyamaibole, Lanieta et al, "An evaluation of Bubble-CPAP in Neonatal Unit in a Developing Country" Journal of Tropical Pediatrics, 2006, pp. 249-253, vol. 52, No. 4.
Nekvasil, R. et al, "High Frequency "Bubble" Oscillation Ventilation in the Neonatal Period" Cesk. Pediatr., 1992, pp. 465-470, vol. 47, No. 8 Abstract.
International Search Authority, Form 206, PCT/US 14/53736 dated Dec. 18, 2014, See p. 2, Form 206(extra Sheet), Consideration regarding Unity of Invention and Obviousness.
International Search Authority, International Search Report and Written Opinion, PCT/US 14/53736 dated Feb. 18, 2015.
Ramanathan, R. et al, "Non-Invasive Ventilation and Surfactant Therapy" J Pulmon Resp Med, 2013, pp. 1-7, vol. S13.
Chan, KM et al., "The Use of Bubble CPAP in Premature Infants: Local Experience", Hong Kong Journal of Paediatrics, Dec. 31, 2007, pp. 86-92, vol. 12, No. 2.
Ammari, Amer et al, "Bubble nasal CPAP manual" Riyadh AL-Kharj Hospital Programme Neonatal Intensive Care 2005, XP-002541077, Dec. 31, 2005.
Lee, Kyong-Soon et al., "A Comparison of Underwater Bubble CPAP with Ventilator-Derived CPAP in Premature Neonates Ready for Extubation" Biol Neonate, 1998, pp. 69-75, vol. 73.
Narendran, Vivek et al., "Early Bubble CPAP and Outcomes in ELBW Preterm Infants", Journal of Perinatology, 2003, pp. 195-199, vol. 23.
Garg, S et al., "Non-Invasive Ventilation in Premature Infants: Based on Evidence or Habit" J. Clin. Neonatology, 2013, pp. 155-159, vol. 2, No. 4.
Diblasi, R, "Nasal Continuous Posistive Airway Pressure (CPAP) for Respiratory Care of Newborn Infant", Selezion Arir de Respiratory Care e AARC Times, 2010, pp. 3-29, No. 1.
Pillow, J. Jane et al., "Bubble CPAP: Is the Noise Important? An In Vitro Study" Pediatric Research, 2005, pp. 826-830, vol. 57, No. 6.
Diblasi, Robert et al, "Noninvasive Respiratory Support of Juvenile Rabbits by High-Amplitude Bubble CPAP" Pediatr Res 2010, pp. 624-629, vol. 67, No. 6.
Diblasi, Robert et al, "Effective Gas Exchange in Paralyzed Juvenile Rabbits Using Simple, Inexpensive Respiratory Support Devices" Pediatr Res 2010, pp. 526-530, vol. 68, No. 6.
India Patent Office, Examination Report, dated Oct. 7, 2020.

* cited by examiner

APPARATUS AND METHOD TO PROVIDE BREATHING SUPPORT

CROSS-REFERENCE TO RELATED APPLICATIONS

This application is a continuation of co-pending U.S. patent application Ser. No. 15/139,020 filed Apr. 26, 2016, which is a continuation-in-part of U.S. patent application Ser. No. 14/468,320, filed Aug. 25, 2014, now U.S. Pat. No. 9,345,850 issued on May 24, 2016, which claims the benefit of the earlier filing dates of U.S. Provisional Patent Application No. 61/874,323, filed Sep. 5, 2013; U.S. Provisional Patent Application No. 61/929,947, filed Jan. 21, 2014; and the above listed patent applications are incorporated herein by reference.

FIELD

Embodiments described herein concern devices and methods that assist gas exchange and stabilize lung volume in patients of all ages with breathing problems.

BACKGROUND

Patients who have breathing difficulties are conventionally provided breathing assistance using mechanical ventilators. These devices are generally expensive and out of reach of a large portion of the population, particularly in economically disadvantaged countries. These devices also require substantial training and expertise to operate and maintain. Further, these devices do not provide the user the ability to set and vary upper limit of safe positive pressure that is patient specific and commensurate with the peak inspiratory pressure levels set during ventilation in an easy and less expensive way.

In recent years, there has been increasing interest in the development of breathing assistance devices that are less expensive. U.S. Pat. No. 8,499,759 discloses the use of a two-way valve in a pressure regulating breathing assistance apparatus wherein the valve is placed intermediate two pressure control conduits that are submerged at varying lengths in a single container containing a fluid. In such apparatus, depending on the size of the valve, back pressure is generated whereby the pressure of gas at a patient interface may be higher than the pressure set using one of the control conduits, but not the other. This back pressure, if not correctly accounted for, has important treatment and safety implications if the device is used on a patient. Further, such apparatus require a container containing a fluid. The use of a container containing fluid may not be practical in certain conditions, e.g., when the patient is in a location where fluid is not readily available or fluid shakes and spills because of motion during transport of patients.

There is a significant need to provide a respiratory assistance apparatus that is easy and less expensive to make, operate and maintain, and has high-positive-pressure safety feature that is simple, reliable and easily adjustable relative to the desired patient-specific inspiratory pressure level.

SUMMARY OF THE INVENTION

It is generally known in the medical profession that stabilization of lung volumes and improvement in gas exchange in patients receiving ventilation assistance could be achieved through appropriate settings and control of the positive pressures generated, amplitude and frequency of oscillating positive pressure in the ventilator. Embodiments described herein provide the user a device and method to set peak inspiratory pressure, positive end-expiratory pressure, breaths per minute, inspiratory time, and further allows the user to set the upper limit of positive pressure that is specific for a patient to reduce the likelihood of damage to the lungs. Additionally, the embodiments described herein maintain a patient's mean airway pressure at controlled levels. Device parameters such as the values of pressures for inhalation and exhalation are adjustable. These embodiments also have features that allow a user to select and modulate breaths per minute, inspiratory time, and the ratio of inspiratory to expiratory time. The embodiments described herein are useful to adults, children and newborn babies. Further, the embodiments can be used during transport of patients, and may be used in facilities that do not have access to mechanical ventilators.

In one embodiment, a ventilator system is provided having a pressurized gas supply, two pressure-relief valves, and a primary duct with two ends—the proximal end and the distal end. The proximal end is connected to the pressurized gas supply. The primary duct is adapted for connection to a patient interface between the proximal and distal ends. A peak inspiratory pressure control duct is connected to the distal end and a first pressure-relief valve is connected to the peak inspiratory pressure control duct. A positive end-expiratory pressure control duct is also connected to the distal end of the primary duct and a second pressure-relief valve is connected to the positive end-expiratory pressure control duct. A two-port valve, also known as a two-way valve, is connected in between the inspiratory pressure control duct and the positive end-expiratory pressure control duct wherein the rate of opening and closing of the valve can be controlled. In addition, at least one safety duct is connected to the primary duct near the proximal end and is connected to a third pressure-relief valve. The value of pressure at which pressure will be relieved using the pressure-relief valve connected to the at least one safety duct is controlled by the user. In some embodiments, pressure-relief valves are adjustable and have simple markings, for example in cm of water, to help the user set high pressure (peak inspiratory pressure), low pressure (positive end-expiratory pressure), and high-pressure limit (Pop-Off). In other embodiments, a pressure-relief valve is adjusted by rotating a knob connected to the valve or by pressing buttons that send signal to the pressure-relief valve to deliver high and low pressures. In yet another embodiment, the pressure-relief valve is adjusted using a signal from a programmable controller. In certain embodiments, as a safety feature, the default position of the ventilator system is to deliver the lower pressure at all times as CPAP when the ventilator system is connected to the patient.

In another embodiment, a pressure-relief valve is connected to the PIP control duct and the PEEP control duct is immersed in a liquid column inside a container. In yet another embodiment, a pressure-relief valve is connected to the PEEP control duct and the PIP control duct is immersed in a liquid column inside a container. In some embodiments, two-way or three-way valve allows the user to set breathing rates from 4-60 per minute, known as conventional mechanical breaths. In other embodiments, the breathing rates are in the range of 60-900 per minute, known as high frequency range. In yet another embodiment, a controller allows the user to control inspiratory to expiratory ratios or have it fixed as percent of cycle time to maintain a desired inspiration time to expiration time ratio, when the cycle frequencies are adjusted. Valves used in the embodiments include without limitation solenoid valves, pneumatic valves and solar powered valves.

In another embodiment, a ventilator system is provided having a pressurized gas supply, two pressure-relief valves, and a primary duct with two ends—the proximal end and the distal end. The proximal end is connected to the pressurized gas supply. The primary duct is adapted for connection to a patient interface between the proximal and distal ends. Also provided is a three-port valve (also known as a three-way valve) having one inlet port and two outlet ports. The distal end of the primary duct is connected to the inlet port of the valve. The first outlet port of the valve is connected to a peak inspiratory pressure control duct that is connected to a first pressure-relief valve. The second outlet port of the valve is connected to a positive end-expiratory pressure control duct that is connected to a second pressure-relief valve. In operation, the valve alternatively connects the inlet port to the first outlet port and the second outlet port, i.e., the gas entering the inlet port passes through the first outlet port for a period of time and then the gas entering the inlet port passes through the second outlet port for another period of time, completing a cycle of passage of gas through the first outlet port and the second outlet port. The cycle then repeats. A controller communicably connected to the valve controls the number of cycles per unit time, for example, number of cycles per minute. In addition, at least one safety duct is connected to the primary duct near the proximal end and is connected to a third pressure-relief valve that is set at a value greater than the value set for the pressure-relief valve connected to the peak inspiratory pressure control duct.

In another embodiment, the pressure-relief valves are mechanical and the level at which pressure will be relieved is set by a mechanical device, e.g., a knob that is connected to the valve. In another embodiment, the pressure-relief valves are electro-mechanical and the level at which pressure will be relieved is set by a controller that sends a signal to the pressure-relief valve. In yet another embodiment, the pressure-relief valve is a pneumatic valve or a solenoid valve. In one embodiment, the pressure relief valve is a variable pressure-relief valve in which the value of pressure at which a pressure relief occurs can be varied.

In some embodiments, the peak inspiratory pressure control duct and the end-expiratory pressure control duct are substantially circular having an inside diameter of between about 0.5 to 2 cm and the pressure-relief valves are adjustable in the pressure range of about 0-50 cm H2O.

DETAILED DESCRIPTION

Embodiments described herein provide the user a device and method to set high and low pressures, oscillations, amplitude and frequency and further allows the user to set the upper limit of positive pressure that is specific for a patient to reduce the likelihood of damage to the lungs. Device parameters such as pressure value at which the pressure-relief valve will activate, level of fluid in a container, length of the duct immersed in the fluid in the container can be varied to control the pressures. In another embodiment, a system may not use a duct immersed in a fluid in a container for pressure control, and all pressures are controlled by pressure-relief valves. In some embodiments, pressure regulators or pressure control valves may be used instead of a pressure-relief valve. For example, a diaphragm pressure regulator may be used instead of a pressure-relief valve. In the present description, a reference to a pressure-relief valve also refers to any valve such as a pressure regulator that can control pressure upstream of the valve.

Figure 1:
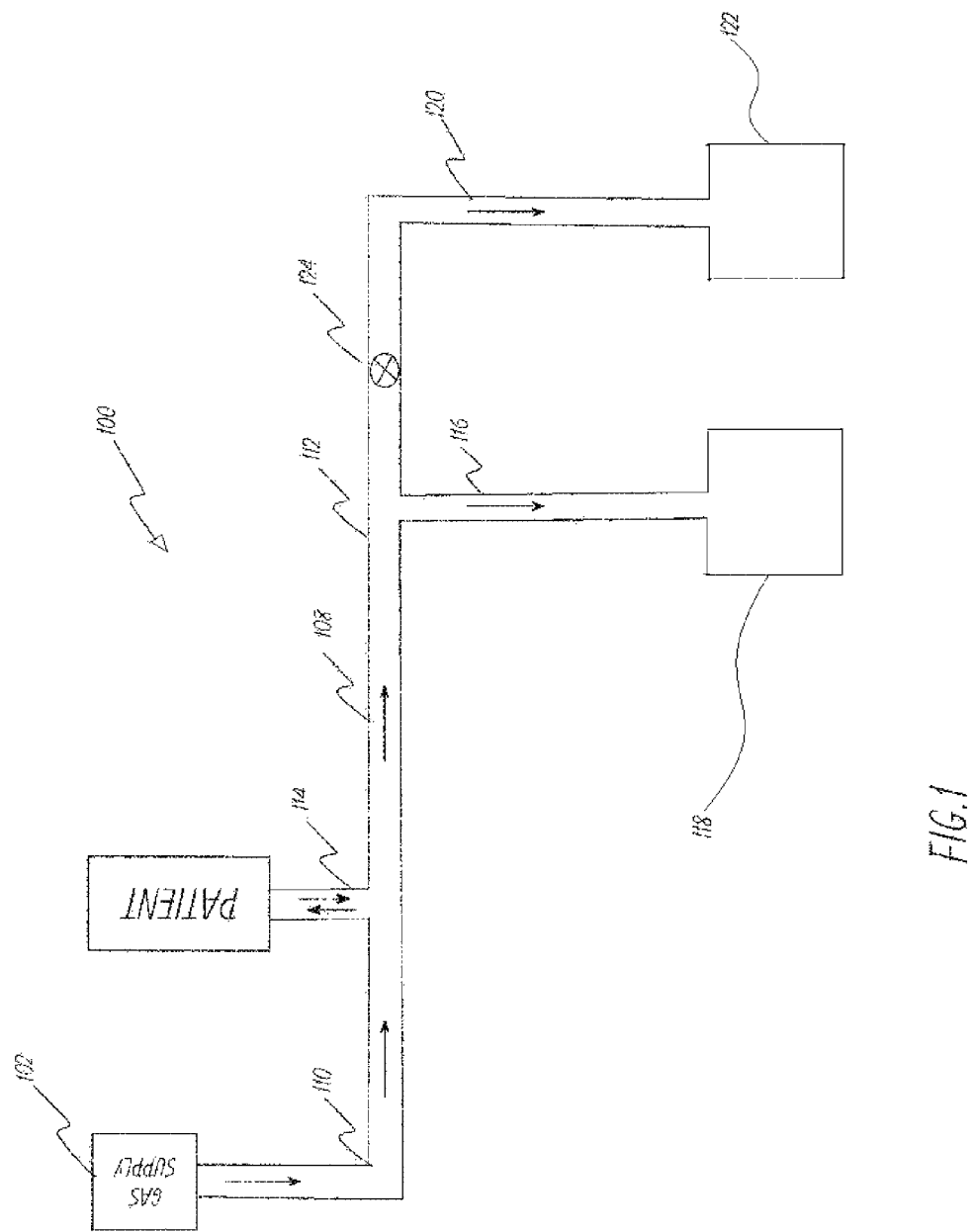
FIG. 1 depicts a ventilator system utilizing a peak inspiratory pressure control duct connected to a first pressure-relief valve; a positive end-expiratory pressure control duct connected to a second pressure-relief valve; and one two-port valve located in-between the peak inspiratory pressure control duct and the positive end-expiratory pressure control duct. Based on the durations of valve open and shut times, low as well high frequency breathing support can be delivered at fixed or variable ratio of inspiratory to expiratory time.

The embodiments described herein also have features that allow the user to select and modulate breaths per minute, inspiratory time, and the ratio of inspiratory to expiratory time. The embodiments are useful for patients of all ages including adults, children and newborn babies. Further, the embodiments can be used during transport of patients of all ages and in facilities that do not have access to mechanical ventilators. In operation, pressurized gas is released from the gas supply into the primary duct of an embodiment described herein, and the gas is delivered to a patient FIG. 1 illustrates a patient ventilation system 100 having a pressurized gas supply 102, two pressure-relief valves 118 and 122, and a primary duct 108 with two ends—the proximal end 110 and the distal end 112. The proximal end 110 is connected to the pressurized gas supply 102. The duct 108 is adapted for connection to a patient interface 114 between the proximal end 110 and distal end 112. At the distal end 112, at least one peak inspiratory pressure (PIP) control duct 116 is connected. The proximal end of the PIP control duct 116 is connected to the distal end 112 of the primary duct 108. The distal end of the PIP control duct 116 is connected to a pressure-relief valve 118. At least one positive end-expiratory pressure (PEEP) control duct 120 is also connected to the distal end 112 of the primary duct 108. The proximal end of the PEEP control duct 120 is connected to the distal end 112 of the primary duct 108. The distal end of the PEEP control duct 120 is connected to a pressure-relief valve 122. A two-port valve 124 is connected in between the inspiratory pressure control duct and the positive end-expiratory pressure control duct. The valve 124 cycles from open to shut position and back to open position, and the rate of cycling of the valve can be controlled by a controller (not shown) communicably connected to the valve. The failure mode of the valve 124 is the open position whereby the gas flow is directed to the positive end expiratory pressure (PEEP) control duct 120 and the pressure at the patient interface 114 is maintained at the lower or baseline level.

In some embodiments of the PIP and PEEP control ducts, the diameters of the ducts are about 0.5 cm to 2 cm. In other embodiments, more than one PIP control duct and more than one PEEP control duct may be used. In yet other embodiments, the PIP and PEEP control ducts may each have substantially similar lengths and diameters or different lengths and diameters. The lengths and cross-sectional shapes of the primary duct, the PIP control duct, and the PEEP control duct are preferably short and substantially circular or slightly oval in shape. However, any or all of the ducts can have any length or cross-sectional shape including but not limited to square, rectangular, triangular etc., without departing from the spirit of the present disclosure.

A gas supply provides pressurized medical grade gas to the ventilator system including to the primary duct, patient duct, PIP control duct and PEEP control duct. Gas delivered by the gas supply may comprise atmospheric gases or any combination, mixture, or blend of suitable gases, including but not limited to atmospheric air, oxygen, nitrogen, helium, or combinations thereof. The gas supply may comprise a gas compressor, a container of pressurized gases, a substantially portable container of pre-pressurized gases, a gas-line hookup (such as found in a hospital) or any other suitable supply of pressurized gas, or combinations thereof. The gas supply is preferably controlled or configured to have a variable gas flow rates that can be controlled by user and adjusted according to the individual requirements of each patient. The patient ventilation system or gas supply may also include one or more flow control devices (not shown) including but not limited to a mechanical valve, an electronically controlled mechanical valve, a rotameter, a pressure regulator, a flow transducer, or combinations thereof. Gas flow rates, which are commonly used in the art, typically range from about 2 liters/minute (L/min) to about 15 L/min. However, these embodiments allow any flow rates of gas set by the user. For example, larger patients may require larger gas flows. Increasing the flow rates could result in the delivery of higher pressures; however, by setting the high-pressure blow-out level of the safety duct to a safe level, one can avoid inadvertent delivery of excessively high pressures to the patient.

A Heat and Moisture Exchanger (not shown) can also be included in the patient ventilation system to control the temperature and humidity of gas delivered to the patient interface. Continuous flow of gas in the delivery duct also prevents the patient from re-breathing gases exhaled from the lungs.

Referring to FIG. 1, the patient interface 114 can be invasive or non-invasive, including but not limited to face or nasal masks, nasal prongs, nasal cannula, short tube(s) placed in the nasal or naso-paharynx, endotracheal tubes, tracheostomy tubes, or combinations thereof. The two-port valve 124 may comprise a mechanical or electromechanical valve. The two-port valve 124 may be electronically controlled or mechanically controlled such that the user is able to set the ventilation rate and inspiratory time or the ratio of inspiratory to expiratory time. The two-port valve 124 is preferably "normally open" such that in the event of failure the valve would remain open and the patient would be subjected to the lower or baseline pressure. When the two-port valve 124 is open, gases flow through PEEP control duct 120 to PEEP pressure-relief valve 122, which is set to relieve pressure at a level lower than the set level of PIP pressure-relief valve 118 thereby controlling the positive end expiratory pressure in the circuit. When the two-port valve 124 is closed, gas in the pressurized circuit flows through PIP control duct 116 to PIP pressure-relief valve 118, which is set to relieve pressure at a level higher than the set level of PEEP pressure-relief valve 122, thereby raising the pressure to peak inspiratory pressure and delivering a "mandatory breath" to the patient. The valve 124 can then be opened again to allow the patient to exhale, and the process may be repeated. In this manner, a patient can receive peak inspiratory pressure and positive end expiratory pressure (Bi-PAP ventilation) or intermittent positive pressure ventilation (IPPV). In some embodiments, any number of valves, PIP control ducts and PEEP control ducts can be used to provide different levels of high and low pressures. In another embodiment, the PIP and PEEP pressure-relief valves may be directly and/or logically connected to a controller (not shown) associated with the system. In one embodiment, each of a movement of PIP valve, PEEP valve, and the two-way valve is controlled by controller. In one embodiment, controller contains machine-readable program instructions as a form of non-transitory tangible media.

Figure 2:
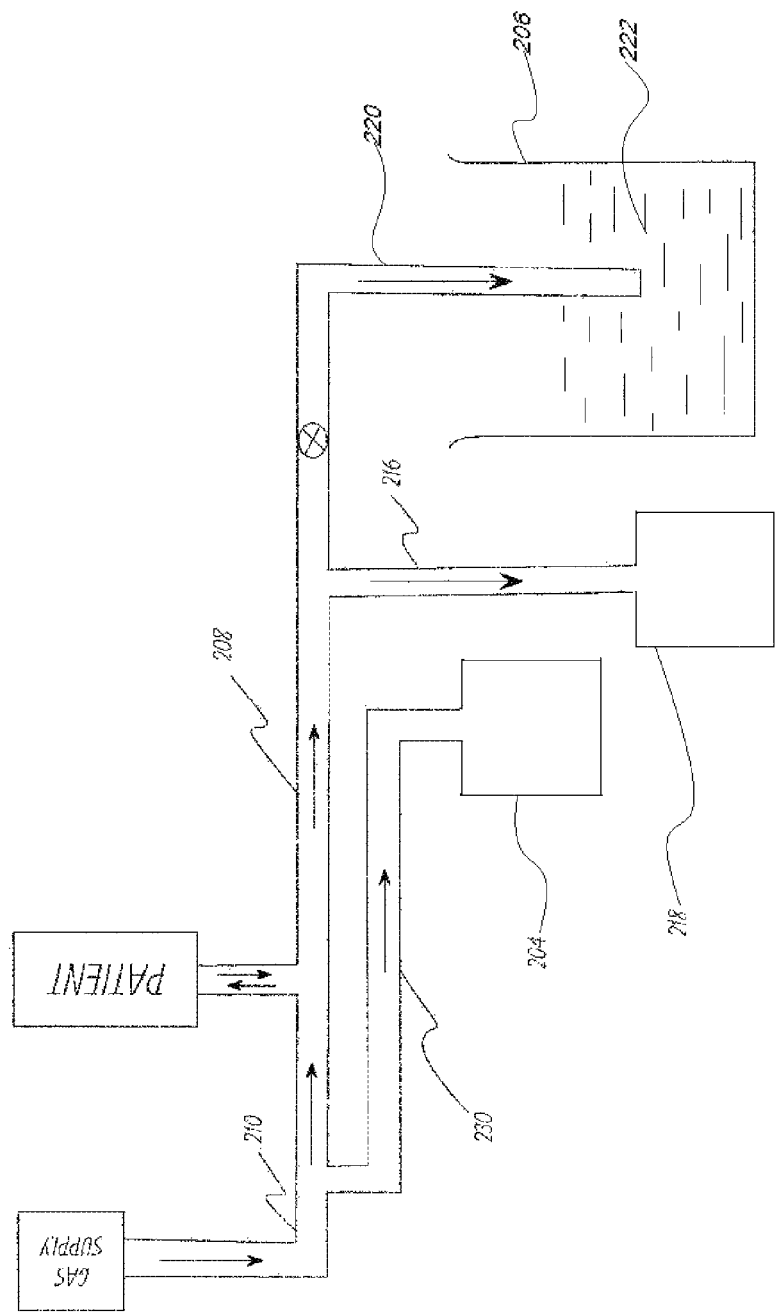
FIG. 2 depicts a ventilator system utilizing a peak inspiratory pressure control duct connected to a first pressure-relief valve; a positive end-expiratory pressure control duct immersed in a fluid in a container; one two-port valve located in-between the peak inspiratory pressure control duct and the positive end-expiratory pressure control duct; and one high pressure safety duct connected to a second pressure-relief valve.

FIG. 2 illustrates a ventilator system similar to FIG. 1, the difference being the PEEP safety relief valve 122 of FIG. 1 is replaced with a container 206 having a fluid 222. In addition, the ventilator system of FIG. 2 has at least one safety duct 230. The safety duct 230 is connected to the primary duct 208 near the proximal end 210 of the primary duct 208. The safety duct 230 is connected to a pressure-relief valve 204 which is set at a level of pressure greater than the level of pressure set in the PIP pressure-relief valve 218. The safety duct allows setting the limit of a safe pressure relative to the set PIP pressure. For example, in some embodiments the safety pressure-relief valve 204 is set to relieve pressure at a level that is 5 cm of water higher than the set level of pressure in the PIP pressure-relief valve 218, if the user wants the maximum pressure that the lungs may be subjected to be not greater than the set PIP pressure by 5 cm of water.

The fluid 222 may comprise any number of suitable fluids or liquids exhibiting a wide range of densities, masses and viscosities including but not limited to water, or water with added vinegar to reduce the likelihood of bacterial contamination of the water. In certain embodiments, the peak inspiratory pressure control duct 216 and the positive end-expiratory pressure control duct 220 are substantially circular having an inside diameter of between about 0.5-2 cm. The immersed length inside the container is in the range of about 2-50 cm. The immersed vertical length of PEEP control duct 220 can be measured as the vertical distance from the fluid surface to the distal ends of the ducts. In all embodiments, the immersed vertical length of the PEEP control duct 220 can be adjusted to any value by adding or removing fluid to adjust fluid level, by sliding the ducts up and down to adjust the duct location, or doing both. The set level of PEEP pressure corresponds to the immersed vertical length of the PEEP control duct 220.

Figure 3:
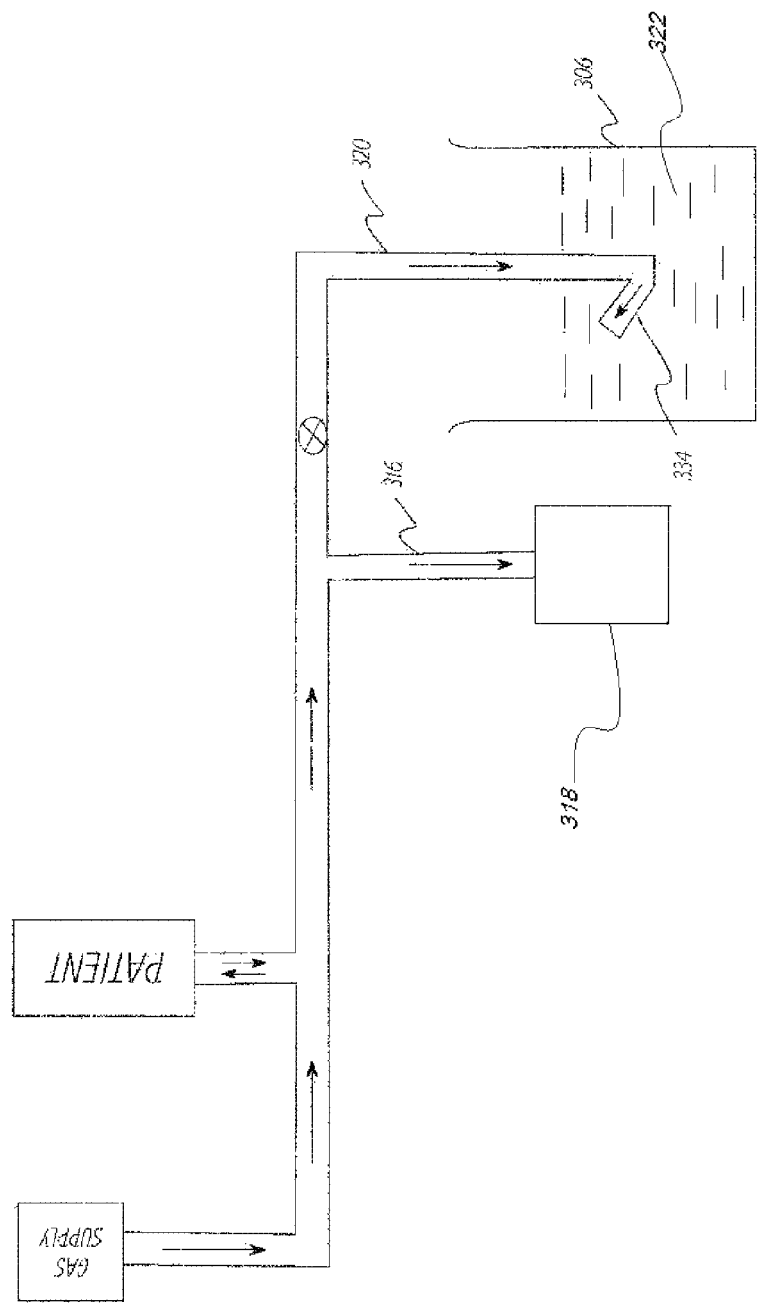
FIG. 3 depicts a ventilator system as shown in FIG. 2 without the high pressure safety duct and with an angled portion added to the positive end-expiratory pressure control duct.

FIG. 3 illustrates a patient ventilator system similar to that illustrated in FIG. 2 utilizing a PIP control duct 316, a PIP pressure-relief valve 318, a PEEP control duct 320 in the container 306, except that the system in FIG. 3 does not have a safety duct and a safety valve as shown in FIG. 2. The duct 320 is immersed in fluid 322 and configured to modulate airway pressures in a patient receiving Bi-PAP or IPPV. The embodiment illustrated in FIG. 3 further comprises an angled section 334 connected to the distal ends of the PEEP control duct. The angle of angled section may be altered between 0 and 180 degrees to the vertical to control the amplitude and frequency of airway pressure oscillations that are superimposed on top of the airway pressure wave form for the exhalation cycle. In some embodiments, the angled arm of the angled section has length of between 2 cm and 10 cm. In other embodiments, more than two angled sections may be used. In one embodiment, the angles of the two or more angled sections may be substantially similar. In other embodiments, the angles of the two or more angled sections may be different. In one embodiment, the diameter of the angled section is the same as the diameter of the PEEP control duct. In another embodiment, the diameter of the angled section is different from the diameter of the PEEP control duct. The immersed vertical length of PEEP control duct can be measured as the vertical distance from the fluid surface to the elbow of the angled section.

Figure 4:
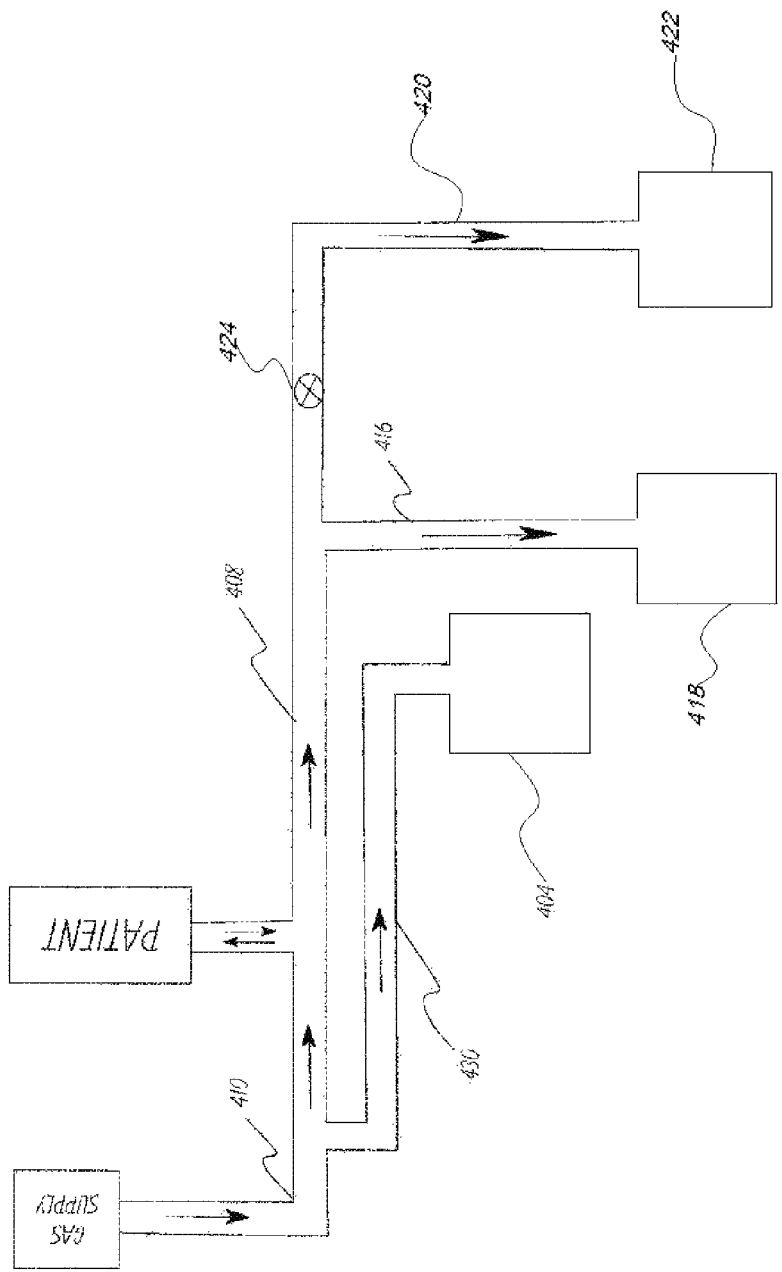
FIG. 4 depicts a ventilator system as shown in FIG. 1 with an addition of one high pressure safety duct connected to a third pressure-relief valve.

FIG. 4 illustrates a ventilator system similar to FIG. 1, but has in addition, at least one safety duct 430. The safety duct 430 is connected to the primary duct 408 near the proximal end 410 of the primary duct 408. The safety duct 430 is connected to a pressure-relief valve 404 which is set at a level of pressure greater than the level of pressure set in the PIP pressure-relief valve 418 that is connected to PIP control duct 416. The safety duct allows setting the limit of a safe pressure relative to the set PIP pressure.

In another embodiment, the PEEP pressure-relief valve 422 may be absent and the gas coming out of the PEEP duct 420 is released directly to the atmosphere without passing through a PEEP pressure-relief valve. The PEEP pressure of the ventilator system then corresponds to the back-pressure of the two-port valve 424. The PEEP pressure in this embodiment would be equal to the back pressure of the valve 424 at the flow rate of gas in the ventilator system.

Figure 5:
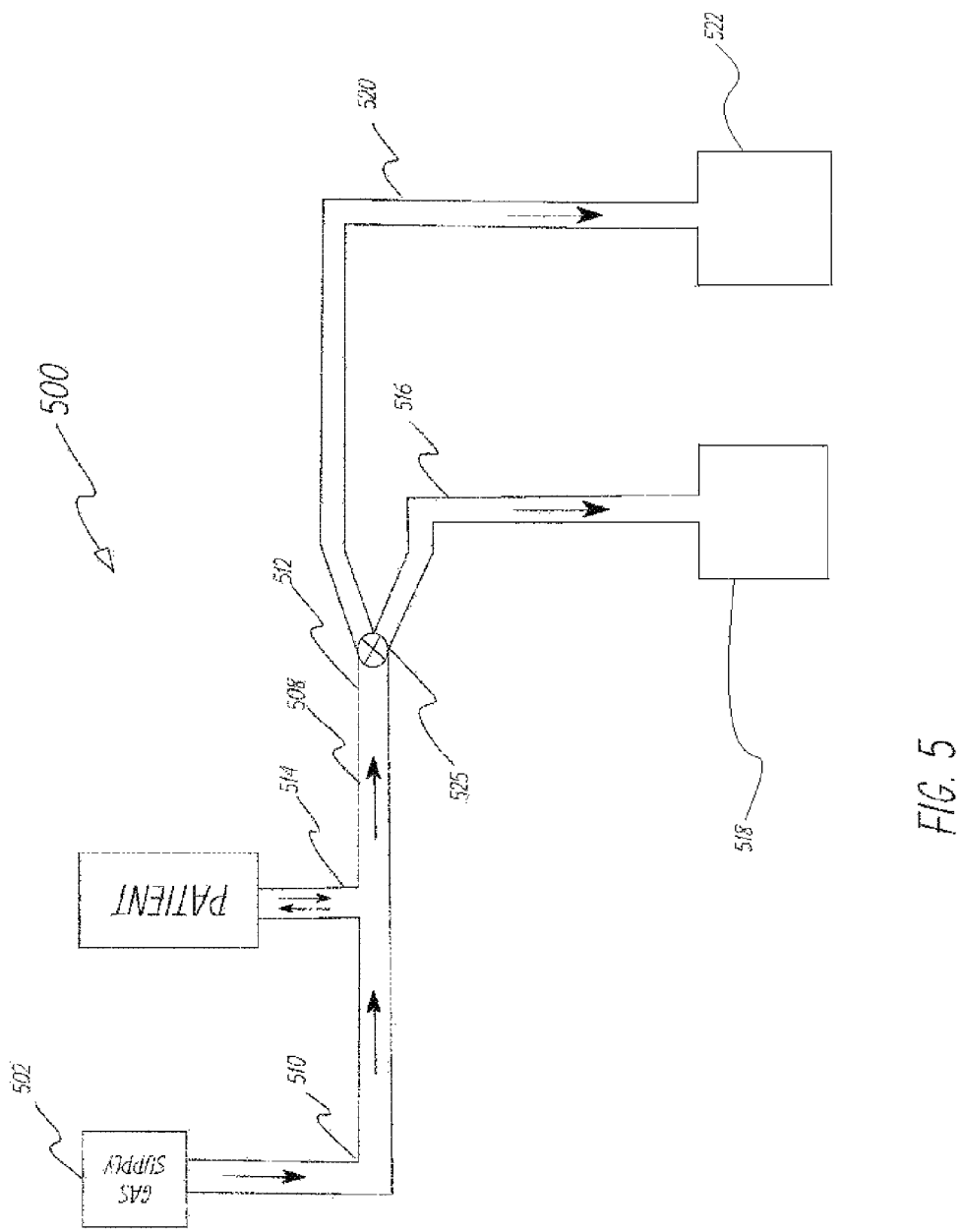
FIG. 5 depicts a ventilator system utilizing a peak inspiratory pressure control duct connected to a first pressure-relief valve; a positive end-expiratory pressure control duct connected to a second pressure-relief valve; one three-port valve connected to the peak inspiratory pressure control duct, the positive end-expiratory pressure control duct and a primary duct.

FIG. 5 illustrates a patient ventilator system 500 having a pressurized gas supply 502, two pressure-relief valves 518 and 522, and a primary duct 508 with two ends—proximal end 510 and distal end 512. The proximal end 510 is connected to the pressurized gas supply 502. The primary duct 508 is adapted for connection to a patient interface 514 between the proximal end 510 and distal end 512. A three-port (also known as three-way) valve 525 is provided with one inlet port and two outlet ports. The distal end 512 is connected to the inlet port of the three-port valve 525. The first outlet port of the valve 525 is connected to at least one peak inspiratory pressure (PIP) control duct 516. A proximal end of the PIP control duct 516 is connected to the first outlet port of the valve 525 and the distal end of the PIP control duct 516 is connected to a PIP pressure-relief valve 518. The second outlet port of the valve 525 is connected to at least one positive end-expiratory pressure (PEEP) control duct 520. The proximal end of the PEEP control duct 520 is connected to the second outlet port of the valve 525. The distal end of the PEEP control duct 520 is connected to a PEEP pressure-relief valve 522.

The valve 525 cycles between the first outlet port and the second outlet port thereby continuously switching the flow of gas from the inlet port to the first outlet port and the inlet port to the second outlet port. Each cycle corresponds to one breath. In operation, when the gas flows from the inlet port to the first outlet port of valve 525, gas flows through PIP control duct 516 to the PIP pressure-relief valve 518, which is set at a level of pressure higher than the level of pressure set in the PEEP pressure-relief valve 522, thereby controlling the PIP in the circuit. When the gas flows from the inlet port to the second outlet port of valve 525, gas in the pressurized circuit flows through PEEP control duct 520 to the PEEP pressure-relief valve 522, which is set at a level of pressure lower than the level of pressure set in the PIP pressure-relief valve 518, thereby lowering the pressure to PEEP and allowing the patient to exhale. The valve 525 can then cycle back to the first outlet port to allow the patient to receive PIP, and the cycle may be repeated. In this manner, a patient can receive peak inspiratory pressure and positive end expiratory pressure (Bi-PAP ventilation) or intermittent positive pressure ventilation (IPPV).

In one embodiment, rate of cycling (measured in cycles per minute) of the valve 525 is controlled using a controller (not shown) communicably connected to the valve. In another embodiment, controller allows user to set time T1 (Inspiratory Time) during which gas flows from the inlet port to the first outlet port and time T2 (Expiratory Time) during which gas flows from the inlet port to the second outlet port. In one embodiment, T1 is set as time in seconds. In another embodiment, T1 or T2 can be set as a fraction of cycle time or as a ratio of T1 and T2 such that the sum of T1 and T2 equals time of one cycle. Because the PIP control duct is connected to the first outlet port and the PEEP control duct is connected to the second outlet port, T1 is inspiratory time and T2 is expiratory time of a cycle or breath. In one embodiment, the expiratory time T2 is set to be greater than inspiratory time T1, and the ratio T2/T1 is greater than 1. The ratio of inspiratory time and expiratory time may be depicted as T1:T2 and the ratio shown as 1:N where, in one embodiment, N is a number greater than 1. In another embodiment, the controller does not allow the value of N to be less than 1. In another embodiment, breaths per minute (bpm) and inspiratory time (T1) in seconds are set by the user, and the controller calculates expiratory time (T2) in seconds using the formula T2=(60/bpm)−T1. In yet another embodiment, if the calculated expiratory time (T2) in seconds is less than the inspiratory time (T1) in seconds set by the user, the controller sets T1=T2=30/bpm. In another embodiment, controller allows the user to control the ratio of inspiratory time T1 to expiratory time T2 or have T1 fixed as percent of cycle time to maintain a desired inspiration time to expiration time ratio. For example, if T1 is set as 33% of cycle time, then T2 will be 67% of cycle time, giving T1:T2 ratio of 1:2. In another embodiment, the controller is integrated with the valve, with the control logic embedded in the valve. In one embodiment, the failure mode of the valve 525 is the open position to the second outlet port whereby the gas flow is directed to the PEEP control duct 520 and the pressure in the ventilator system is maintained at the baseline, i.e. lower level. In another embodiment, if the controller sets the cycling rate of the valve 525 as zero, the valve remains in the open position to the second outlet port whereby the gas flow is directed to the PEEP control duct 520 and the pressure in the ventilator system is maintained at the baseline i.e. lower level. In another embodiment, if power to the valve 525 is shut off, the valve remains in the open position to the second outlet port whereby the gas flow is directed to the PEEP control duct 520 and the pressure in the ventilator system is maintained at the baseline i.e. lower level. Thus the apparatus can be converted from Bi-PAP ventilation to CPAP by simply shutting off power to the valve or setting cycling rate of the valve to zero.

In one embodiment, the pressure-relief valves 518 and 522 are mechanical. The level of pressure at which the pressure relief will occur is set manually using a knob or a dial. In another embodiment, the pressure-relief valves are electro-mechanical. The level of pressure at which the pressure relief will occur is set using a controller. Depending on the level set in the controller at which the pressure relief is to occur, the controller sends a signal to valve whereby the valve adjusts the valve position and opening to the required level of pressure relief.

Figure 6:
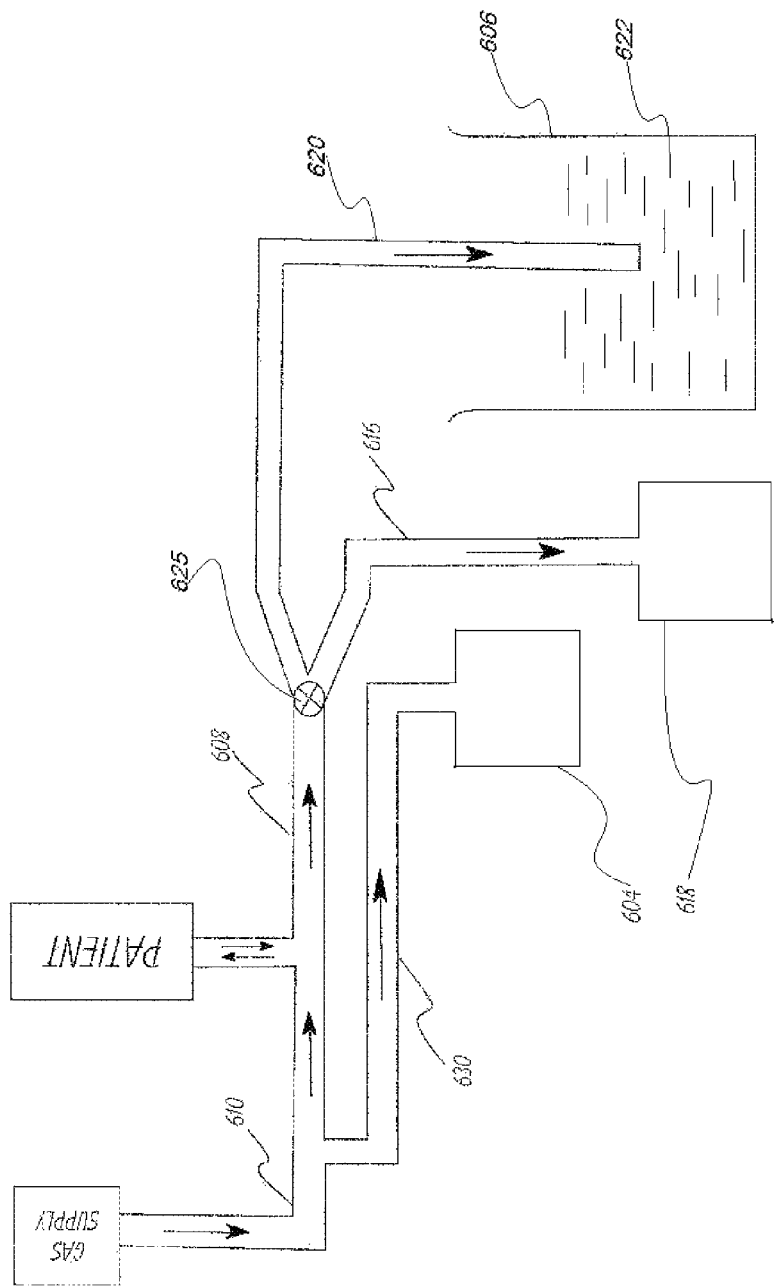
FIG. 6 depicts a ventilator system utilizing a peak inspiratory pressure control duct connected to a first pressure-relief valve; a positive end-expiratory pressure control duct immersed in a fluid in a container; one three-port valve connected to the peak inspiratory pressure control duct, the positive end-expiratory pressure control duct and a primary duct; one high pressure safety duct connected to a second pressure-relief valve.

FIG. 6 illustrates a ventilator system similar to FIG. 5, the difference being the PEEP pressure-relief valve 522 of FIG. 5 is replaced with a container 606 having a fluid 622. In addition, the ventilator system of FIG. 6 has at least one safety duct 630. The safety duct 630 is connected to the primary duct 608 near the proximal end 610 of the primary duct 608. The safety duct 630 is connected to a pressure-relief valve 604 which is set at a level of pressure greater than the level of pressure set in the PIP pressure-relief valve 618. The safety duct allows setting the limit of a safe pressure relative to the set PIP pressure. For example, in some embodiments the safety pressure-relief valve 604 is set to relieve pressure at a level that is 5 cm of water higher than the set level of pressure in the PIP pressure-relief valve 618, if the user wants the maximum pressure that the lungs may be subjected to be not greater than the set PIP pressure by 5 cm of water.

The fluid 622 may comprise any number of suitable fluids or liquids exhibiting a wide range of densities, masses and viscosities including but not limited to water, or water with added vinegar to reduce the likelihood of bacterial contamination of the water. In certain embodiments, the valve 625 is connected to the peak inspiratory pressure control duct 616 and the end-expiratory pressure control duct 620 which are substantially circular having an inside diameter of between about 0.5-2 cm. The immersed length inside the container is in the range of about 2-50 cm. The immersed vertical length of PEEP control duct 620 can be measured as the vertical distance from the fluid surface to the distal ends of the ducts. In all embodiments, the immersed vertical length of the PEEP control duct 620 can be adjusted to any value by adding or removing fluid to adjust fluid level, by sliding the ducts up and down to adjust the duct location, or doing both. The set level of PEEP pressure corresponds to the immersed vertical length of the PEEP control duct.

Figure 7:
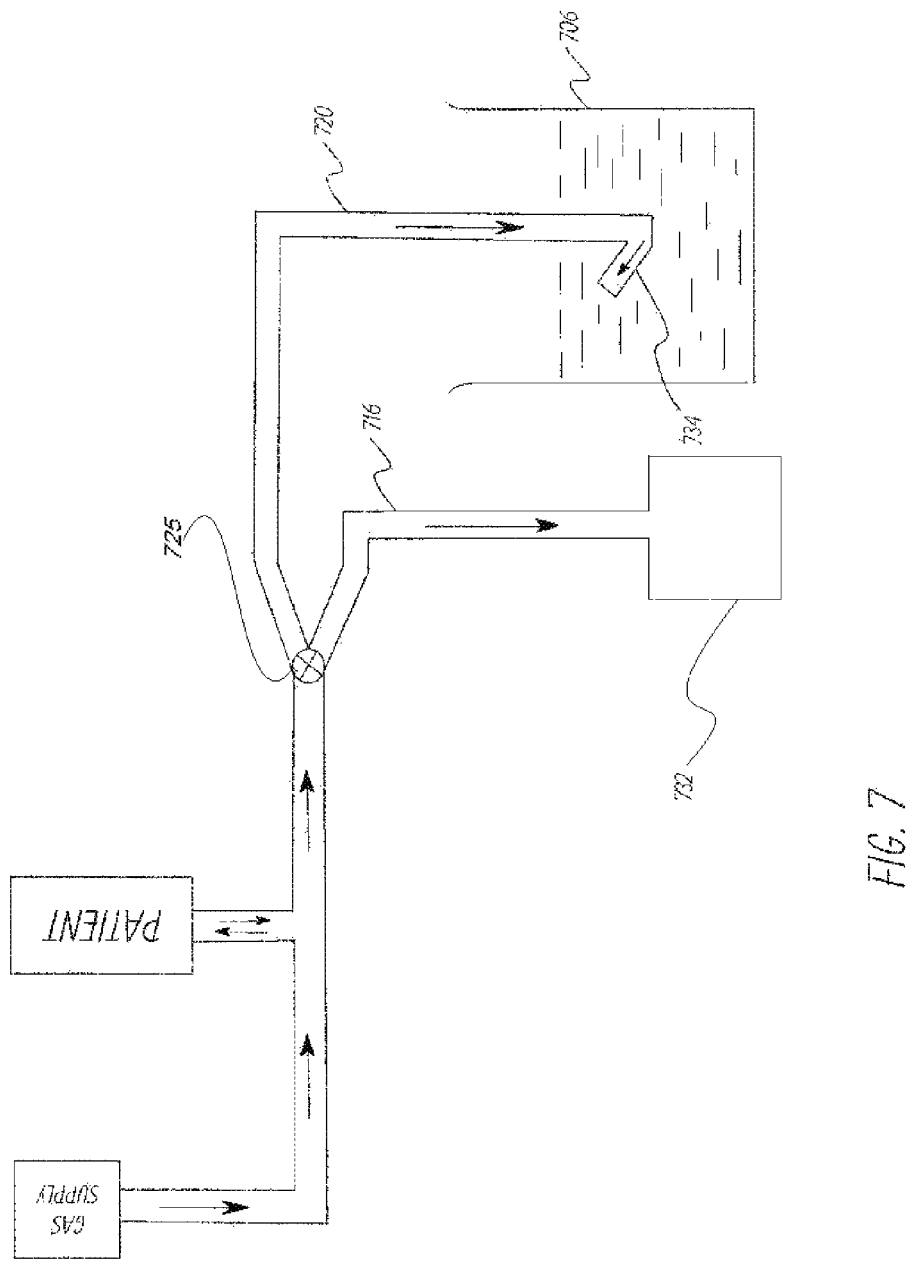
FIG. 7 depicts a ventilator system as shown in FIG. 6 without the high pressure safety duct and with an angled portion added to the positive end-expiratory pressure control duct.

FIG. 7 illustrates a ventilator system similar to that illustrated in FIG. 6 utilizing a valve 725, a PIP control duct 716, a PIP pressure-relief valve 732, and a PEEP control duct 720 in the container 706, except that the system in FIG. 7 does not have a safety duct and a safety valve as shown in FIG. 6. The duct 720 is immersed in fluid and configured to modulate airway pressures in a patient receiving Bi-PAP or IPPV. The embodiment illustrated in FIG. 7 further comprises an angled section 734 connected to the distal end of the PEEP control duct. The angle of angled section may be altered between 0 and 180 degrees to the vertical to modify the amplitude and frequency of airway pressure oscillations that are superimposed on top of the airway pressure wave form for both the exhalation cycle. In some embodiments, the angled arm of the angled section has length of between 2 cm and 10 cm. In some embodiments, more than two angled sections may be used. In other embodiments, the angles of the two or more angled sections may be substantially similar. In still other embodiments, the angles of the two or more angled sections may be different.

Figure 8:
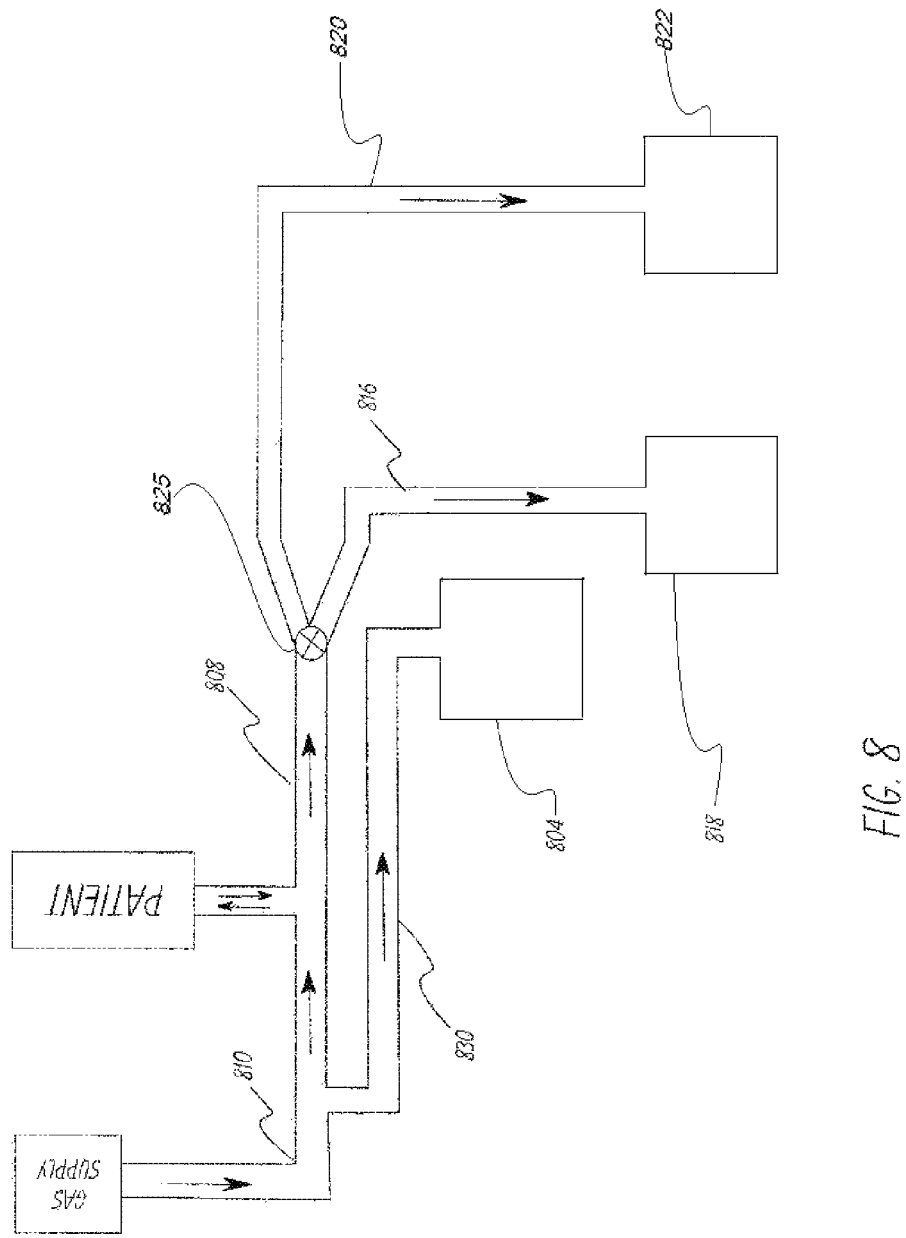
FIG. 8 depicts a ventilator system as shown in FIG. 5 with an addition of one high pressure safety duct connected to a third pressure-relief valve.

FIG. 8 illustrates a ventilator system similar to FIG. 5, but has in addition, at least one safety duct 830. The safety duct 830 is connected to the primary duct 808 near the proximal end 810 of the primary duct 808. The safety duct 830 is connected to a pressure-relief valve 804 which is set at a level of pressure greater than the level of pressure set in the PIP pressure-relief valve 818 that is connected to PIP control duct 816. The safety duct allows setting the limit of a safe pressure relative to the set PIP pressure.

In another embodiment, the PEEP pressure-relief valve 822 is absent and the gas coming out of the PEEP duct 820 is released directly to the atmosphere without passing through a PEEP pressure-relief valve. The PEEP pressure of the ventilator system then corresponds to the back-pressure of the three-port valve 825. The PEEP pressure in this embodiment would be equal to the back pressure of the valve 825 at the flow rate of gas in the ventilator system.

In addition to the safety duct illustrated in FIGS. 2, 4, 6 and 8, some embodiments can include additional safety features (not shown) such as a high pressure "pop-off" or "pop-open" safety valve to protect the patient from receiving airway pressures greater than a pre-determined threshold to reduce the likelihood of high pressures reaching the patient in the unlikely event that the patient circuit is occluded between the patient and the gas exiting the system through the fluid container. The pop-off valve provides a second level of protection when the safety duct such as duct 230 in FIG. 2 is present in the ventilator system. The pressure level setting of pop-off valve will be generally higher than the blow-out pressure setting of the safety duct. Note however that pop-off safety valve is generally pre-set to certain values and does not provide user the flexibility provided by the safety duct, which allows setting the limit of safe pressure relative to the set PIP pressure.

Figure 9:
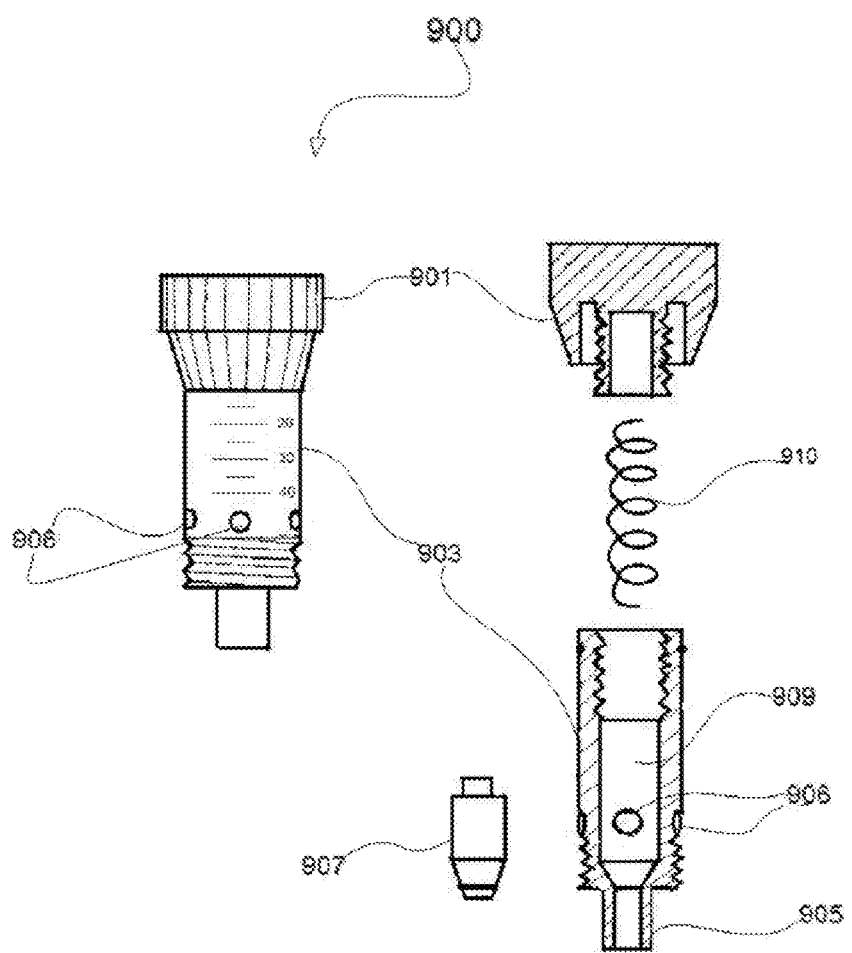
FIG. 9 depicts a spring-loaded pressure-relief valve.

FIG. 9 shows an embodiment of a pressure-relief valve. The pressure-relief valve 900 can be set to control pressure of gas upstream of the valve. A knob 901 is rotated manually clockwise or counter-clockwise to set the pressure at which the pressure relief will occur. The relief pressure is set by rotating the knob to appropriate pressure marking on the body of the valve 903. In another embodiment, the pressure markings are on a circular dial around the top perimeter of the knob. The gas enters the valve 900 at the inlet port 905 and exits the valve at outlet ports 906. A float 907 is placed in a cavity 909 inside the body of the valve 903 with the conical end of the float aligned with the conical end of the cavity 909. A spring 910 is then placed in the cavity 909 on top of the float and in between the float and the knob 901. In one embodiment, when the knob 901 is rotated clockwise, the spring 910 compresses on the float 907 thereby pressing it against the entrance of the valve. Depending on the pressure of the gas entering the valve 900, the spring is pushed back, thereby releasing the gas through outlet ports 906 and maintaining a gas pressure in the system upstream of the valve. The valve can be made of plastic or metals such as brass and steel. In other embodiments of the ventilator system, a diaphragm pressure regulator may be used instead of the spring pressure-relief valve.

Figure 10:
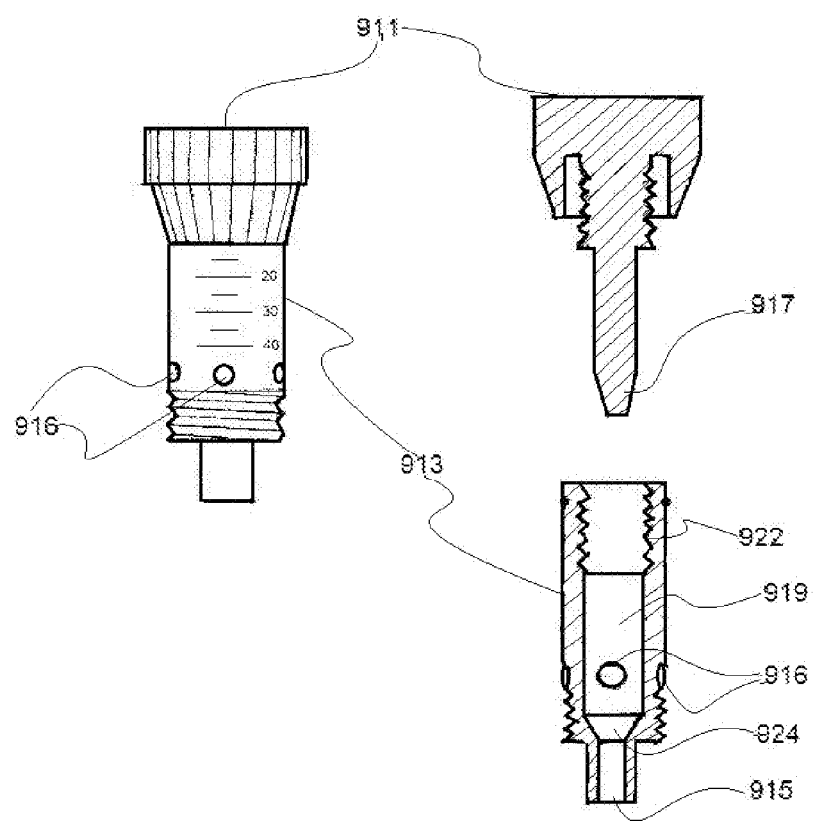
FIG. 10 depicts a manually adjusted pressure-relief valve.

FIG. 10 shows an embodiment of pressure-relief valve similar to the pressure-relief valve in FIG. 9 with the gas entering the valve at the inlet port 915 and exiting the valve at outlet ports 916, except that the valve in FIG. 10 does not have a spring. In FIG. 10, the float 917 is directly connected to the knob 911 and is an integral part of the knob. When the knob 911 is screwed into the body 913, the float 917 takes a position inside the cavity 919 of the valve. The location of the float 917 inside the cavity 919 depends on the number of times the knob is rotated on threads 922. Depending on the location of the float 917, there remains a gap between the float 917 and the cone 924 inside the cavity 919. This gap offers a resistance to the gas entering the valve at the inlet port 915. The upstream pressure of the gas can be set by adjusting the size of the gap which in turn is done by rotating the knob 911. In another embodiment, the pressure-relief valve may be directly and/or logically connected to a controller associated with the system, and the movement of pressure-relief valve is controlled by the controller. In one embodiment, controller contains machine-readable program instructions as a form of non-transitory tangible media.

Some embodiments can include a low-pressure "pop-open" or one-way valve (not shown) to protect the patient from receiving airway pressures lower than a pre-determined threshold, for example sub-atmospheric pressures. In this manner, the one-way valve can help prevent a lung from collapsing, help prevent the patient from inhaling fluid, and help prevent the patient from re-breathing exhaled gases. Fresh gas of controlled concentration (not shown) can also be supplied to the one-way valve.

Figure 11:
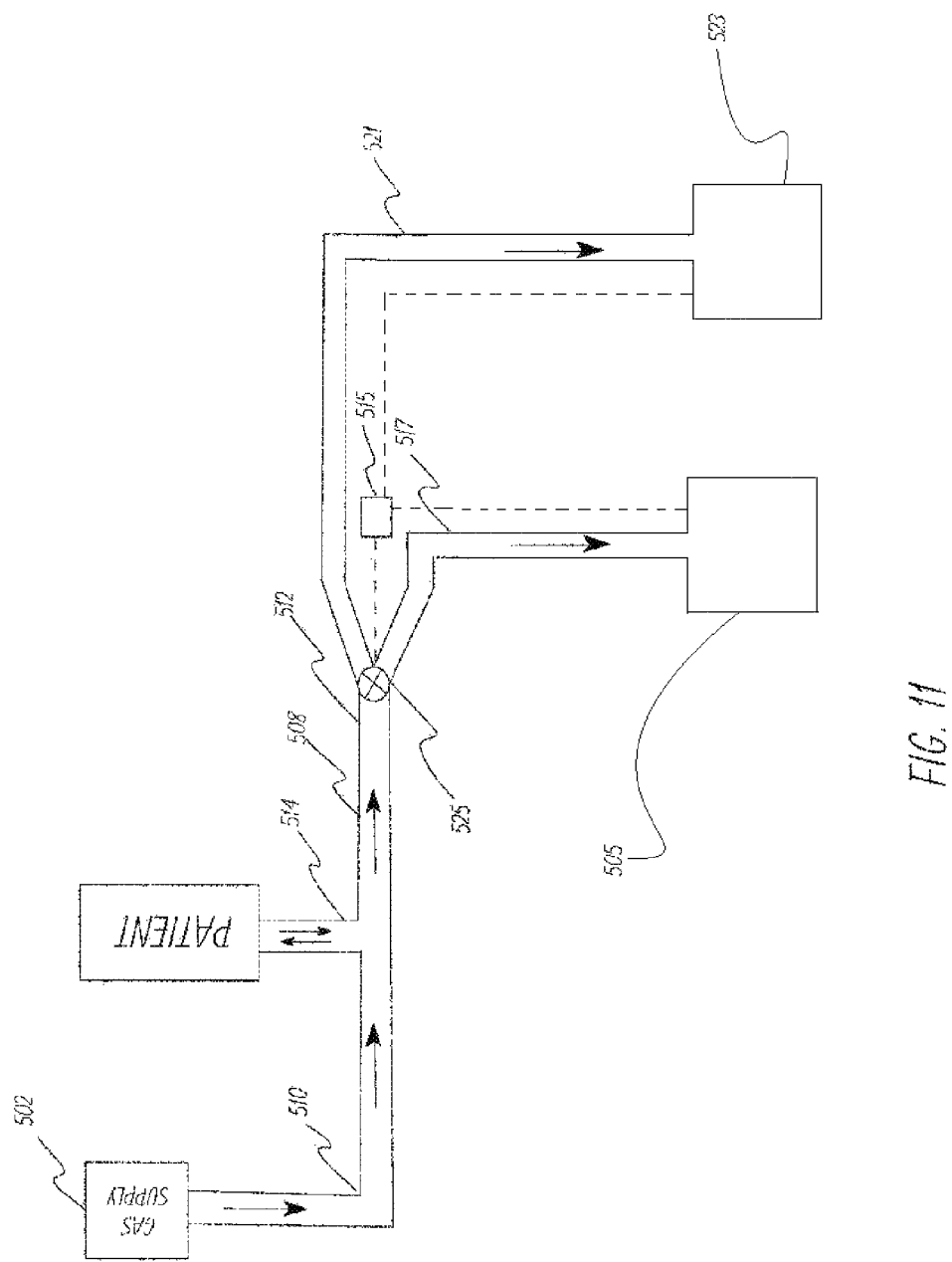
FIG. 11 depicts a ventilator system utilizing a peak inspiratory pressure control duct connected to a first pressure-relief valve; a positive end-expiratory pressure control duct connected to a second pressure-relief valve; one three-port valve connected to the peak inspiratory pressure control duct, the positive end-expiratory pressure control duct and a primary duct; and a controller communicably connected to the three-port valve, the first pressure-relief valve, and the second pressure-relief valve.

FIG. 11 illustrates a patient ventilator system having a pressurized gas supply 502, two pressure-relief valves 505 and 523, and a primary duct 508 with two ends—proximal end 510 and distal end 512. The proximal end 510 is connected to the pressurized gas supply 502. The primary duct 508 is adapted for connection to a patient interface 514 between the proximal end 510 and distal end 512. A three-port (also known as three-way) valve 525 is provided with one inlet port and two outlet ports. The distal end 512 is connected to the inlet port of the three-port valve 525. The first outlet port of the valve 525 is connected to at least one peak inspiratory pressure (PIP) control duct 517. A proximal end of the PIP control duct 517 is connected to the first outlet port of the valve 525 and the distal end of the PIP control duct 517 is connected to a PIP pressure-relief valve 505. The second outlet port of the valve 525 is connected to at least one positive end-expiratory pressure (PEEP) control duct 521. The proximal end of the PEEP control duct 521 is connected to the second outlet port of the valve 525. The distal end of the PEEP control duct 521 is connected to a pressure-relief valve 523.

The valve 525 cycles between the first outlet port and the second outlet port thereby continuously switching the flow of gas from the inlet port to the first outlet port and the inlet port to the second outlet port. Each cycle corresponds to one breath. In operation, when the gas flows from the inlet port to the first outlet port of valve 525, gas flows through PIP control duct 517 to the PIP pressure-relief valve 505, which is set at a level of pressure higher than the level of pressure set in the PEEP pressure-relief valve 523, thereby controlling the PIP in the circuit. When the gas flows from the inlet port to the second outlet port of valve 525, gas in the pressurized circuit flows through PEEP control duct 521 to the PEEP pressure-relief valve 523, which is set at a level of pressure lower than the level of pressure set in the PIP pressure-relief valve 505, thereby lowering the pressure to PEEP and allowing the patient to exhale. The valve 525 can then cycle back to the first outlet port to allow the patient to receive PIP, and the cycle may be repeated. In this manner, a patient can receive peak inspiratory pressure and positive end expiratory pressure (Bi-PAP ventilation) or intermittent positive pressure ventilation (IPPV).

In one embodiment, rate of cycling (measured in cycles per minute) of the valve 525 is controlled using a controller 515 communicably connected to the valve. In another embodiment, controller 515 allows user to set time T1 (Inspiratory Time) during which gas flows from the inlet port to the first outlet port and time T2 (Expiratory Time) during which gas flows from the inlet port to the second outlet port. In one embodiment, T1 is set as time in seconds. In another embodiment, T1 or T2 can be set as a fraction of cycle time or as a ratio of T1 and T2 such that the sum of T1 and T2 equals time of one cycle. Because the PIP control duct is connected to the first outlet port and the PEEP control duct is connected to the second outlet port, T1 is inspiratory time and T2 is expiratory time of a cycle or breath. In one embodiment, the expiratory time T2 is set to be greater than inspiratory time T1, and the ratio T2/T1 is greater than 1. The ratio of inspiratory time and expiratory time may be depicted as T1:T2 and the ratio shown as 1:N where, in one embodiment, N is a number greater than 1. In another embodiment, the controller 515 does not allow the value of N to be less than 1. In another embodiment, breaths per minute (bpm) and inspiratory time (T1) in seconds are set by the user, and the controller 515 calculates expiratory time (T2) in seconds using the formula T2=(60/bpm)−T1. In yet another embodiment, if the calculated expiratory time (T2) in seconds is less than the inspiratory time (T1) in seconds set by the user, the controller 515 sets T1=T2=30/bpm. In another embodiment, controller 515 allows the user to control the ratio of inspiratory time T1 to expiratory time T2 or have T1 fixed as percent of cycle time to maintain a desired inspiration time to expiration time ratio. For example, if T1 is set as 33% of cycle time, then T2 will be 67% of cycle time, giving T1:T2 ratio of 1:2. In another embodiment, the controller 515 is integrated with the valve, with the control logic embedded in the valve.

In one embodiment, the failure mode of the valve 525 is the open position to the second outlet port whereby the gas flow is directed to the PEEP control duct 521 and the pressure in the ventilator system is maintained at the baseline, i.e. lower level. In another embodiment, if the controller 515 sets the cycling rate of the valve 525 as zero, the valve remains in the open position to the second outlet port whereby the gas flow is directed to the PEEP control duct 521 and the pressure in the ventilator system is maintained at the baseline i.e. lower level. In another embodiment, if power to the valve 525 or the controller 515 is shut off, the valve remains in the open position to the second outlet port whereby the gas flow is directed to the PEEP control duct 521 and the pressure in the ventilator system is maintained at the baseline i.e. lower level. Thus the apparatus can be converted from Bi-PAP ventilation to CPAP by simply shutting off power to the valve or setting cycling rate of the valve to zero. In one embodiment, the controller 515 is connected to the three-port valve 525 with wires, and the controller 515 communicates with the three-port valve 525 through the wires. In another embodiment, the controller 515 communicates with the three-port valve 525 wirelessly and communication between the three-port valve 525 and the controller 515 can be achieved using any of the generally known wireless protocols. In another embodiment, the PIP pressure-relief valve 505 and the PEEP pressure-relief valve 523 may be directly and/or logically connected to controller 515 associated with the system. In one embodiment, each of a movement of PIP valve 505, PEEP valve 523 and the three-way valve 525 is controlled by controller 515. In one embodiment, controller contains machine-readable program instructions as a form of non-transitory tangible media. In another embodiment, controller may be directly and/or logically connected to a monitoring device that monitors the vitals such as blood oxygen level and blood pressure of a patient. In yet another embodiment, controller may communicate with an iDevice such as iPad or iPhone, and the settings of the controller can be monitored and adjusted using the iDevice.

In one embodiment, the pressure-relief valves 505 and 523 are mechanical. The level of pressure at which the pressure relief will occur is set manually using a knob or a dial. In another embodiment, the pressure-relief valves are electro-mechanical. The level of pressure at which the pressure relief will occur is set using the controller 515. Depending on the level of pressure set in the controller 515 at which the pressure relief is to occur, the controller sends a signal to the pressure-relief valve whereby the valve adjusts the position and opening of the valve to the required level of pressure relief. In one embodiment, the controller 515 is connected to the pressure-relief valves 505 and 523 with wires and the controller 515 communicates with the pressure-relief valves 505 and 523 through the wires. In another embodiment, the controller 515 communicates with the pressure-relief valves 505 and 523 wirelessly and the communication between the pressure-relief valves and the controller is achieved using any of the generally known wireless protocols.

Figure 12:
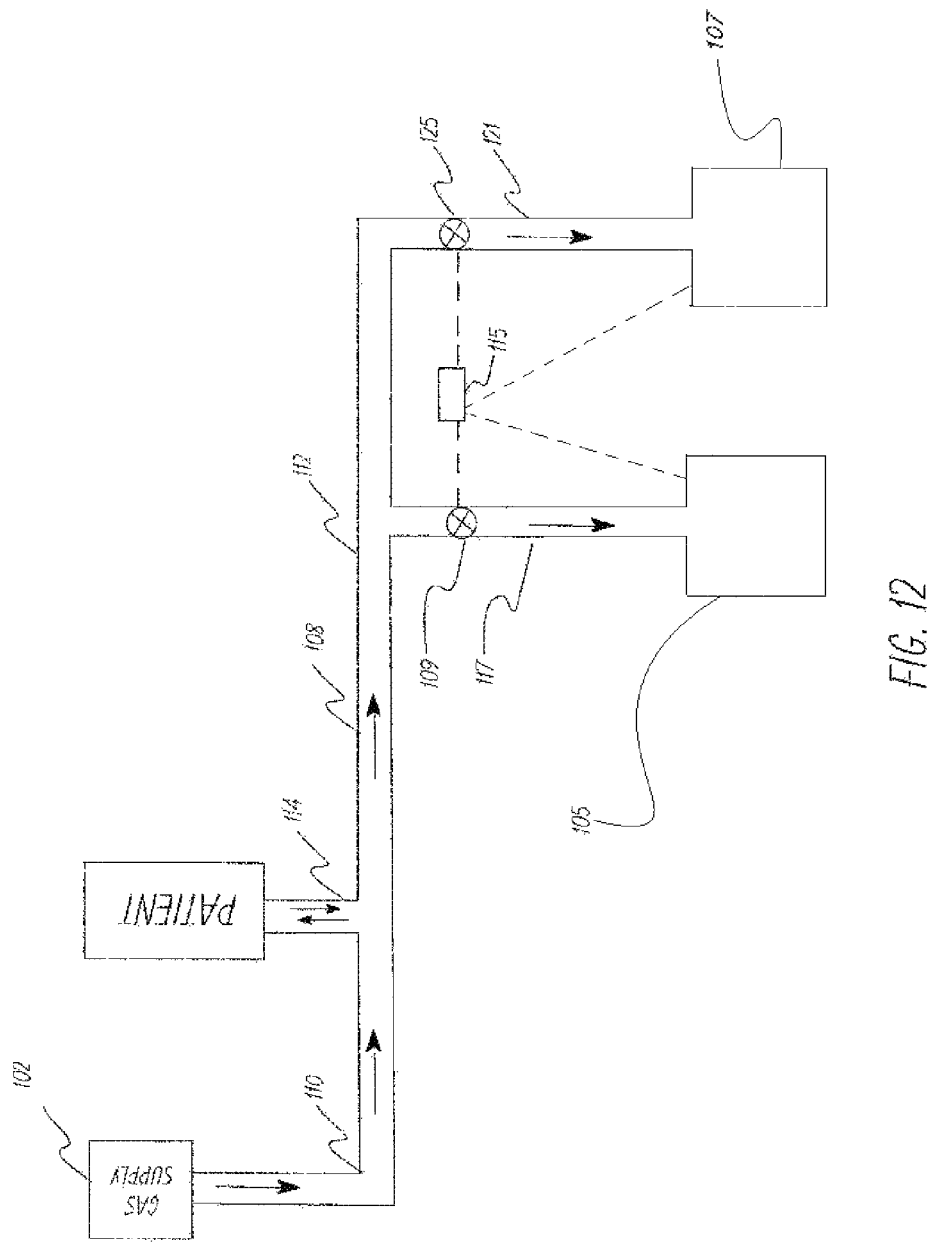
FIG. 12 depicts a ventilator system utilizing a peak inspiratory pressure control duct connected to a first pressure-relief valve; a positive end-expiratory pressure control duct connected to a second pressure-relief valve; one two-port valve located on the positive end-expiratory pressure control duct; one two-port valve located on the peak inspiratory pressure control duct; a controller communicably connected to both the two-port valves, and also communicably connected to the first pressure-relief valve and the second pressure-relief valve.

FIG. 12 illustrates a patient ventilation system having a pressurized gas supply 102, pressure-relief valves 105 and 107, and a primary duct 108 with two ends—the proximal end 110 and the distal end 112. The proximal end 110 is connected to the pressurized gas supply 102. The duct 108 is adapted for connection to a patient interface 114 between the proximal end 110 and distal end 112. At the distal end 112, at least one peak inspiratory pressure (PIP) control duct 117 is connected. The proximal end of the PIP control duct 117 is connected to the distal end 112 of the primary duct 108. The distal end of the PIP control duct 117 is connected to PIP pressure-relief valve 105. At least one positive end-expiratory pressure (PEEP) control duct 121 is also connected to the distal end 112 of the duct. The proximal end of the PEEP control duct 121 is connected to the distal end of the primary duct 108. The distal end of the PEEP control duct 121 is connected to the PEEP pressure-relief valve 107. The PIP pressure-relief valve 105 is set to relieve pressure at a level greater than the level of pressure at which the PEEP pressure-relief valve 107 is set to relieve the pressure. A two-port valve 109 is placed on the PIP control duct 117 and is located between the PIP control duct 117 and the distal end 112 of the primary duct. Another two-port valve 125 is placed on the PEEP control duct 121 and is located between the PEEP control duct 121 and the distal end 112 of the primary duct. The valves 109 and 125 cycle from open to shut position and back to open position, and the rate of cycling of the valves can be controlled by a controller 115 communicably connected to the valves 109 and 125. The valves 109 and 125 are controlled by the controller 115 such that when the valve 109 is open, the valve 125 is closed and when the valve 109 is closed, the valve 125 is open.

In operation, when the two-port valve 125 is open and the two-port valve 109 is closed, gases flow through PEEP control duct 121, thereby controlling the PEEP in the circuit. When the two-port valve 125 is closed and the two-port valve 109 is open, gases in the pressurized circuit flows through PIP control duct 117, thereby raising the pressure to peak inspiratory pressure. The valve 125 can then be opened again and valve 109 closed to allow the patient to exhale, and the process may be repeated. In this manner, a patient can receive peak inspiratory pressure and positive end expiratory pressure (Bi-PAP ventilation) or intermittent positive pressure ventilation (IPPV).

In one embodiment, the controller 115 is connected to the two-port valves 109 and 125 using wires and the controller 115 communicates with the two-port valves 109 and 125 through the wires. In another embodiment, the controller 115 is connected to the two-port valves 109 and 125 wirelessly and communication between the two-port valves and the controller is achieved using any of the generally known wireless protocols. In one embodiment, the pressure-relief valves 105 and 107 are mechanical. The level of pressure at which the pressure relief will occur is set manually using a knob or a dial. In another embodiment, the pressure-relief valves are electro-mechanical. The level of pressure at which the pressure relief will occur is set using the controller 115. Depending on the level of pressure set in the controller 115 at which the pressure relief is to occur, the controller sends a signal to the pressure-relief valve whereby the valve adjusts the position and opening of the valve to the required level of pressure relief. In one embodiment, the controller 115 communicates with the pressure-relief valves 105 and 107 through wires. In another embodiment, the controller 115 communicates with the pressure-relief valves 105 and 107 wirelessly and the communication between the pressure-relief valves and the controller is achieved using any of the generally known wireless protocols.

More embodiments concern methods of using one or more of the aforementioned combinations to assist the breathing of a subject (e.g., an adult, child, infant human being or another mammal). By some approaches, a subject having breathing problems is identified or selected and said subject is connected to one or more of the devices described herein. In some embodiments the subject is attached to the device by nasal prongs and in other embodiments, the subject is attached to the device by face or nasal masks, tube(s) placed in the nasopharynx, endotracheal tubes, tracheostomy tubes, or combinations thereof. Once the subject and device are connected, gas flow is initiated. Preferable gas flows for infants are about 1 to 10 L/min, whereas adults may require gas flows of about 1 to 30 L/min and large mammals may require 1 to 100 L/min or more. Optionally, the frequency, amplitude of cycling pressure, or volume of gas delivered is monitored so as to adjust the breathing assistance for the particular subject. In some embodiments, a patient in need of breathing assistance is selected or identified and a breathing assistance device, as described herein, is selected or identified according to a subject's age, size, or therapeutic need.

Some embodiments include a method for providing continuous positive airway pressure with oscillating positive end-expiratory pressure to a subject by providing any of the devices or apparatuses described herein, releasing gas from the gas supply into the apparatus and delivering the gas to the subject. Other embodiments include a method for increasing the volume of gas delivered to a subject by providing any of the breathing assistance devices or apparatuses described herein, adjusting the angle of the distal end of the duct with respect to a vertical axis and releasing gas from the gas supply into the apparatus to deliver gas to the subject. In some embodiments, the distal end of the duct is adjusted to an angle greater than or equal to between about 91-170 degrees. In other embodiments, the distal end of the duct is adjusted to an angle of about 135 degrees with respect to a vertical axis.

EXAMPLE 1

This example describes the ventilator system used and experiments performed to test the system described in FIG. 5. A lung machine manufactured by Ingmar Medical, Pittsburgh, Pa. (www.ingmarmed.com) was connected at patient interface of the ventilator system. Two different three-port valves were tested. (a) A three-port (three-way) solenoid valve manufactured by MAC Valves, Inc., Wixom, Mich. (www.macvalves.com) was used in the system. (b) A three-port (three-way) solenoid valve custom made with an orifice diameter of 10 mm. The cycling of the valve was controlled using an electronic timer made by IDEC Corporation, Sunnyvale, Calif. (us.idec.com). Compressed air and air/oxygen mixtures were used in the tests. The tubing used was the standard 10 mm plastic tubing used with conventional ventilator systems in a hospital setting. The pressure at the patient interface was measured using a manometer manufactured by Life Design Systems, Inc., Madison, Wis. The manometer had a range of −20 cm of water to +80 cm of water in increments of 1 cm water. Tests were run for gas flow rates from 0.5 L/min through 5 L/min in increments of 0.5 L/min, and from 5 L/min through 15 L/min in increments of 1 L/min. The gas flow rate was set using flowmeter manufactured by Precision Medical, Northampton, Pa. (www.precisionmedical.com). Two variable pressure-relief valves were connected. Each variable pressure-relief valve had a rotatable knob that allowed variation of set pressure by rotation of the knob. A scale allowed easy and accurate adjustment of pressure setting at which a pressure relief would occur. The setting of the PIP pressure-relief valve was varied from 10 to 30 cm of water, and the setting of the PEEP pressure relief valve was varied from 2 to 10 cm of water. The cycling of the three-port valve was done from 1 cycle per minute to 60 cycles per minute. Each cycle corresponds to a breath and thus the tests were conducted from 1 breath per minute to 60 breaths per minute.

The three-port valve manufactured by MAC Valves offers a resistance to flow of gas, resulting in a loss of pressure. The loss of pressure due to the resistance of the three-port valve increased as the flow rate of gas was increased. At gas flow rates of 15 L/min, a pressure loss as high as 4 cm water was observed in the valve, resulting in a back pressure whereby observed PIP and PEEP at patient interface was about 4 cm of water higher than that set by the PIP and PEEP pressure-relief valves. Therefore, depending on the flow rate of gas, a correction to account for the back pressure of the valve had to be made to the values of PIP and PEEP set using the pressure-relief valves. When the back pressure was 4 cm of water, a correction of 4 cm to the setting of pressure-relief valve was made such that actual set value was 4 cm less than the required PIP or PEEP at the patient interface. Thus if the required PEEP at the patient interface is 10 cm of water and the back pressure is 4 cm of water, then the set value of PEEP at the pressure-relief valve is 6 cm Tests using the custom made three-port valve with an orifice diameter of 10 mm showed that the back pressure from this three-port valve was negligible for the above test parameters. The back pressure from the valve is primarily due to size the valve (e.g., diameter of valve orifice through which gas passes, diameter of inlet and outlet passage ways and ports of valve) that creates resistance to flow of gas. The smaller the orifice size, e.g., smaller the diameter, the higher the resistance. To minimize the back pressure and the resulting correction to set values of PIP and PEEP, the size of orifice, the size of internal passage ways, the size of the ports are preferably the same as or similar to the size of the ventilator tubing. The pressure loss in the valve can be calculated using a coefficient of flow (Cv) of the valve. The calculation method is generally known. The pressure loss decreases as the Cv value increases. The gas is a compressible fluid and the Cv value and pressure loss of gas depends on temperature and pressure of the gas. The pressure of the gas in the ventilator system is slightly above atmospheric (2-50 cm of water above atmospheric) and the temperature of the gas in the ventilator system may be kept slightly above room temperature and could be as high as 40 degrees Celsius. For the gas pressure and temperature that are generally prevalent in a ventilator system, the coefficient of flow Cv of the valve is preferably greater than about 1.5 and more preferably greater than about 2.

EXAMPLE 2

This example describes the ventilator system used and tests performed using a system as shown in FIG. 12 wherein two two-port valves were used to determine whether two two-port valves would replicate the system and tests done in Example 1 where a single three-port valve was used. Two two-port solenoid valves manufactured by MAC Valves, Inc., Wixom, Mich. were used in the system. The size of the two-port (two-way) valve was the same as the three-port valve manufactured by MAC Valves, Inc. that was used in part (a) of Example 1. The first two-port solenoid valve was placed on the PIP control duct and is located between the PIP pressure-relief valve and the distal end of the primary duct. The second two-port solenoid valve was placed on the PEEP control duct and is located between the PEEP pressure-relief valve and the distal end of the primary duct. The test parameters were the same as those in Example 1. The two valves were controlled such that when the first valve was open, the second valve was closed and when the first valve was closed, the second valve was open. The two two-port valves were identical and their size including valve orifice and port diameters was the same as that of the three-port MAC valve used in part (a) of Example 1. The observed performance of the system in Example 2 was similar to the performance of the system in Example 1 when MAC valve was used.

There has thus been described a medically and commercially useful method and apparatus for providing breathing support. It is appreciated that though described for a patient, the method and apparatus can be used by a healthy mammal to enhance breathing. It will be appreciated that well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics. The particular embodiments described are not provided to limit the invention, but to illustrate it. Further, as the following claims reflect, inventive aspects may lie in less than all features of a single disclosed embodiment. In another situation, an inventive aspect may include a combination of embodiments described herein or in a combination of less than all aspects described in a combination of embodiments. Thus, the claims following the Detailed Description are hereby expressly incorporated into this Detailed Description, with each claim standing on its own as a separate embodiment of the invention.

The invention claimed is:

1. An apparatus to provide breathing support to a patient comprising:
    a primary duct comprising a proximal end and a distal end, wherein the proximal end is connected to a gas supply, the distal end is connected to a three-port valve, and a patient interface is located between the proximal end and the distal end;
    the three-port valve comprising at least three ports, said three ports comprising an inlet port, a first outlet port and a second outlet port, the inlet port adapted for connection to the patient interface via the primary duct;
    at least one peak inspiratory pressure (PIP) control duct connected to the first outlet port of the three-port valve;
    at least one positive end-expiratory pressure (PEEP) control duct connected to the second outlet port of the three-port valve;
    at least one controller;
    wherein activation of the controller switches the three-port valve to direct flow of a gas through either the PIP control duct or the PEEP control duct, thereby providing PIP and PEEP to the patient;
    wherein deactivation of the controller by shutting off power to the controller or setting a cycle rate of the three-port valve using the controller to a value of zero keeps the three-port valve open to the second outlet port whereby flow of the gas is directed to the PEEP control duct and the patient is provided a baseline pressure; and
    wherein a user can convert the apparatus from Bi-PAP ventilation to CPAP ventilation by shutting off power to the controller or setting the cycle rate of the three-port valve to the value of zero.

2. The apparatus of claim 1, further comprising a container containing a body of fluid, wherein the PEEP control duct is configured to be immersed in the body of fluid in the container.

3. The apparatus of claim 1, further comprising at least one safety duct adapted for connection to the primary duct and configured to be connected to a safety pressure-relief valve.

4. The apparatus of claim 1, wherein the at least one controller is communicably connected to the three-port valve to control a rate of cycling of the valve, thereby controlling a number of breaths per minute, and to control at least one of (a) an inspiratory time in seconds, (b) a ratio of the inspiratory time to an expiratory time, and (c) the inspiratory time as a percentage of a cycle time, thereby maintaining the ratio of the inspiratory time to the expiratory time as determined by the user.

5. The apparatus of claim 1, wherein the three-port valve has a coefficient of flow Cv greater than about 1.5.

6. The apparatus of claim 1, wherein the three-port valve is a solenoid valve.

7. The apparatus of claim 1, wherein a failure mode of the three-port valve is an open position to the second outlet port whereby flow of the gas is directed to the PEEP control duct and the pressure in the apparatus is maintained at a baseline level if the three-port valve fails.

8. The apparatus of claim 1, further comprising at least one PIP pressure-relief valve connected to the PIP control duct and at least one PEEP pressure-relief valve connected to the PEEP control duct.

9. The apparatus of claim 8, wherein the PIP pressure-relief valve is a variable pressure-relief valve.

10. The apparatus of claim 8, wherein the PIP pressure-relief valve and the PEEP pressure relieve valve are selected from a group consisting of electronically controlled electromechanical valves or manually controlled mechanical valves.

11. The apparatus of claim 8, wherein the PIP pressure-relief valve and the PEEP pressure-relief valve are communicably connected to the controller.

12. An apparatus to provide breathing support to a patient comprising:
    a primary duct comprising a proximal end and a distal end, wherein the proximal end is connected to a gas supply, the distal end is connected to a three-port valve, and a patient interface is located between the proximal end and the distal end;
    the three-port valve comprising at least three ports, said three ports comprising an inlet port, a first outlet port and a second outlet port, the inlet port adapted for connection to the patient interface via the primary duct;
    at least one peak inspiratory pressure (PIP) control duct connected to the first outlet port of the three-port valve;
    at least one positive end-expiratory pressure (PEEP) control duct connected to the second outlet port of the three-port valve;
    at least two pressure-relief valves wherein a first pressure-relief valve is connected to the PIP control duct and a second pressure-relief valve is connected to the PEEP control duct, and wherein the PIP pressure-relief valve and the PEEP pressure relieve valve are selected from a group consisting of electronically controlled electromechanical valves or manually controlled mechanical valves;
    at least one controller;
    wherein activation of the controller switches the three-port valve to direct flow of a gas through either the PIP control duct or the PEEP control duct, thereby providing PIP and PEEP to the patient;
    wherein deactivation of the controller by shutting off power to the controller or setting a cycle rate of the three-port valve in the controller to a value of zero keeps the three-port valve open to the second outlet port whereby flow of the gas is directed to the PEEP control duct and the patient is provided a baseline pressure; and wherein a user can convert the apparatus from Bi-PAP ventilation to CPAP ventilation by shutting off power to the controller or setting the cycle rate of the three-port valve to the value of zero.

13. The apparatus of claim 12, further comprising at least one safety duct adapted for connection to the primary duct and configured to be connected to a third pressure relief valve.

14. The apparatus of claim 12, wherein the three-port valve has a coefficient of flow Cv greater than about 1.5.

15. The apparatus of claim 12, wherein the three-port valve is a solenoid valve.

16. The apparatus of claim 12, further comprising a pressurized gas supply.

17. The apparatus of claim 12, wherein a failure mode of the three-port valve is an open position to the second outlet port whereby flow of the gas is directed to the PEEP control duct and the pressure in the apparatus is maintained at a baseline level if the three-port valve fails.

18. The apparatus of claim 12, wherein at least one pressure-relief valve comprises a knob or a dial to vary the pressure at which a relief of pressure will occur.

19. The apparatus of claim 12, wherein the at least one controller is communicably connected to the three-port valve to control a rate of cycling of the valve, thereby controlling a number of breaths per minute, and to control at least one of (a) an inspiratory time in seconds, (b) a ratio of the inspiratory time to an expiratory time, and (c) the inspiratory time as a percentage of a cycle time, thereby maintaining the ratio of the inspiratory time to the expiratory time as determined by the user.

20. The apparatus of claim 19, wherein the PIP pressure-relief valve and the PEEP pressure-relief valve are communicably connected to the controller.

* * * * *